(12) United States Patent
Dunn et al.

(10) Patent No.: US 6,653,107 B2
(45) Date of Patent: *Nov. 25, 2003

(54) METHOD AND KIT FOR EVALUATION OF HIV MUTATIONS

(75) Inventors: James M. Dunn, Scarborough (CA); Jean-Michel Lacroix, Etobicoke (CA)

(73) Assignee: Visible Genetics Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/818,182

(22) Filed: Mar. 27, 2001

(65) Prior Publication Data

US 2003/0165815 A1 Sep. 4, 2003

Related U.S. Application Data

(63) Continuation of application No. 09/418,720, filed on Oct. 15, 1999, now Pat. No. 6,265,152, which is a continuation-in-part of application No. 08/938,641, filed on Sep. 26, 1997, now Pat. No. 6,007,983, and a continuation-in-part of application No. 08/819,912, filed on Mar. 18, 1997, now Pat. No. 5,795,722, and a continuation-in-part of application No. 08/577,858, filed on Dec. 22, 1995, now Pat. No. 5,834,189.

(51) Int. Cl.$^7$ .................. C12P 19/34; C07H 21/04; C12Q 1/68

(52) U.S. Cl. .................. 435/91.1; 435/6; 536/24.33

(58) Field of Search .................. 435/6, 91.1, 91.2, 435/810; 536/24.33

(56) References Cited

U.S. PATENT DOCUMENTS

| | | | |
|---|---|---|---|
| 4,358,535 A | 11/1982 | Falkow et al. .................. 435/5 |
| 4,563,417 A | 1/1986 | Albarella et al. .............. 435/6 |
| 4,683,195 A | 7/1987 | Mullis et al. .................. 435/6 |
| 4,683,202 A | 7/1987 | Mullis .......................... 435/91 |
| 4,942,124 A | 7/1990 | Church .......................... 435/6 |
| 4,962,020 A | 10/1990 | Tabor et al. .................... 435/6 |
| 5,008,182 A | 4/1991 | Sninsky et al. ................. 435/5 |
| 5,124,247 A | 6/1992 | Ansorge ......................... 435/6 |
| 5,171,534 A | 12/1992 | Smith et al. ............. 422/82.05 |
| 5,176,995 A | 1/1993 | Sninsky et al. ................. 435/6 |
| 5,219,727 A | 6/1993 | Wang et al. .................... 435/6 |
| 5,283,171 A | 2/1994 | Manos et al. .................... 435/5 |
| 5,296,349 A | * 3/1994 | Wallace ......................... 435/6 |
| 5,403,707 A | 4/1995 | Atwood et al. ................. 435/5 |
| 5,409,810 A | 4/1995 | Larder |
| 5,427,911 A | 6/1995 | Ruano et al. ................... 435/6 |
| 5,451,512 A | 9/1995 | Apple et al. ............... 435/91.2 |
| 5,453,355 A | 9/1995 | Birkenmeyer et al. ......... 435/6 |
| 5,545,527 A | 8/1996 | Stevens |
| 5,629,153 A | 5/1997 | Urdea |
| 5,631,128 A | * 5/1997 | Kozal et al. .................... 435/5 |
| 5,789,153 A | * 8/1998 | Falkner et al. .................. 435/5 |
| 5,795,722 A | 8/1998 | Lacroix |
| 5,834,189 A | 11/1998 | Stevens |
| 5,861,242 A | * 1/1999 | Chee et al. ..................... 435/5 |
| 6,265,152 B1 | * 7/2001 | Dunn et al. ..................... 435/5 |

FOREIGN PATENT DOCUMENTS

| | | |
|---|---|---|
| WO | 9215711 | 9/1992 |
| WO | 9219771 | 11/1992 |
| WO | WO 93 13223 | 7/1993 |
| WO | WO 97 23650 | 7/1997 |
| WO | 9723650 | 7/1997 |
| WO | WO 97 24974 | 7/1997 |

OTHER PUBLICATIONS

Stefan Wiemann, et al; Slmultaneou On–Line DNA . . . ; May 31, 1994; pp. 117–121.*
Vasudevachari et al., Antimicrobial Agents and Chemotherapy 40(11), 2535–2541 (1996).*
Sarkar et al., "Dideoxy Fingerprinting (ddF): A Rapod and Efficient Screen for the Presence of Mutations" *Genomics* 13: 441–443 (1992).
Lin et al., "Characterization of Genetic Defects of Hemophilia A in Patients of Chinese Origin" *Genomics* 18: 496–504 (1993).
Langemeir et al, "Application of Cycle of Dideoxy Fingerprinting to Screening Heterogerous Populations of the Equine Infectious Anemia Virus", *BioTechniques* 17: 484–490 (1994).
Krishnamani et al., "Detection of a Novel Arginine Vasopressin Defect by Dideoxy Fingerprinting" *J. Clin. Endocrinol. & Metabol.* 77: 596–598 (1993).
Nelson et al., "Sequencing two DNA templates in five channels by digital compression", *Proc. Nat'l Acad/ Sci. (USA)* 90: 1647–1651 (1993).
Ansorge et al., "One Label, one tube, Sanger DNA sequencing in one and two lanes on a gel", *Nucl. Acids Res.* 18: 3419–3420 (1990).
Negri et al., "A Single–Reaction Method for DNA Sequence Determinaiton" *Anal. Biochem* 197: 389–395 (1991).
Schinazi et al., "Mutation in retroviral genes associated with drug resistance", *Int'l Antiviral news* 5: 129–142 (1997).
Chamberlain et al., "Detection of Gene Deletions Using Multiplex Polymerase Chain Reactions", *Meth. Molec. Biol.* 9: 299–312 (1991).
Ellison et al., "Detection of Mutations and Polymorphisms Using Fluorescence–Based Dideoxy Fingerprinting (F–ddF)", *Biotechniques* 17: 742–753 (1994).
Eisenstein, B.I., "The Polymerase Chain reaction", *New Engl. J. Med.* 322: 178–183 (1990).
Murakawa et al., "Direct Detection of HIV–1 RNA from AIDS and ARC Patient Samples", *DNA* 7: 287–295 (1988).
Ruano et al., "Coupled Amplification and Sequencing of Genomic DNA", *Proc. Nat'l Acad Sci (USA)* 88: 2815–2819 (1991).

(List continued on next page.)

Primary Examiner—Kenneth R. Horlick
(74) *Attorney, Agent, or Firm*—Oppedahl & Larson LLP

(57) ABSTRACT

A method for obtaining information about the allelic type of a sample of genetic material derived from an HIV-infected sample relies on the observation that using a second nested set of sequencing primers ensures the maximum potential for sequencing a particular sample. To perform the method, reagents suitable for performing the tests are suitably packaged as a kit.

2 Claims, 1 Drawing Sheet

OTHER PUBLICATIONS

Frenkel, L.M., et al., "Specific, Sensitive, and Rapid Assay for Human Immunodeficiency Virus Type 1 pol Mutations Associated with Resistance to Zidovudine and Didanosine", Journal of Clinical Microbiology, vol 33, No. 2, pp 342–347, Feb. 1995.

Sanger, F., et al., "DNA Sequencing with Chain–Terminating Inhibitors", Proc. Natl. Acad. Sci. USA, vol. 74, No. 12, pp. 5463–5467, Dec. 1977.

Kretz, K., et al., "Cycle Sequencing", PCR Methods and Applications, vol. 3, No. 5, pp. S107–S112, Apr. 1994.

Wiemann, S., et al., "Simultaneous On–Line DNA Sequencing on Both Strands with Two Fluorescent Dyes", Analytical Diochemistry, vol. 224, No. 1, pp. 117–121, Jan. 1995.

Haas, J., "Detection, Differentiation and Typing of Human Immunodeficiency Virus by Polymerase Chain Reaction", Springer, Berlin, Germany, 1995, pp. 13–18.

Wahlberg, J., et al., "Automated Magnetic Preparation of DNA Templates for Solid Phase Sequencing", Electrophoresis, vol. 13, pp. 547–551, 1992.

Larder, et al., Nature 365, 671–673, 1993.

* cited by examiner

METHOD AND KIT FOR EVALUATION OF HIV MUTATIONS

This application is a continuation of U.S. patent application Ser. No. 09/418,720 filed Oct. 15, 1999, U.S. Pat. No. 6,265,152, which is a continuation-in-part of U.S. patent application Ser. No. 08/938,641 filed Sep. 26, 1997, U.S. Pat. No. 6,007,983, and a CIP U.S. patent application Ser. No. 08/577,858 filed Dec. 22, 1995, U.S. Pat. No. 5,834,189, and CIP U.S. patent application Ser. No. 08/819,912 filed Mar. 18, 1997, U.S. Pat. No. 5,795,722, which are incorporated herein by reference.

BACKGROUND OF THE INVENTION

Genetic testing to determine the presence of or a susceptibility to a disease condition offers incredible opportunities for improved medical care, and the potential for such testing increases almost daily as ever increasing numbers of disease-associated genes and/or mutations are identified. A major hurdle which must be overcome to realize this potential, however, is the high cost of testing. This is particularly true in the case of highly polymorphic genes where the need to test for a large number of variations may make the test procedure appear to be so expensive that routine testing can never be achieved.

Testing for changes in DNA sequence can proceed via complete sequencing of a target nucleic acid molecule, although many persons in the art believe that such testing is too expensive to ever be routine. Changes in DNA sequence can also be detected by a technique called 'single-stranded conformational polymorphism" ("SSCP") described by Orita et al., Genomics 5: 874–879 (1989), or by a modification thereof referred to a dideoxy-fingerprinting ("ddF") described by Sarkar et al., Genomics 13: 4410443 (1992). SSCP and ddF both evaluate the pattern of bands created when DNA fragments are electrophoretically separated on a non-denaturing electrophoresis gel. This pattern depends on a combination of the size of the fragments and of the three-dimensional conformation of the undenatured fragments. Thus, the pattern cannot be used for sequencing, because the theoretical spacing of the fragment bands is not equal.

This application relates to a particular test which can be useful as part of a testing protocol for the detection and characterization of human immunodeficiency virus (HIV).

SUMMARY OF THE INVENTION

The method of the invention provides a method for obtaining information about the allelic type of a sample of genetic material derived from an HIV-infected sample. A test is performed in which the sequence is determined in the 3'-direction for all four bases. This test will identify substantially all of the samples in which the sequence of the sample is determined in both the 3' and 5-direction for all four bases.

To perform the method of the invention, reagents suitable for the tests are suitably packaged as a kit. The kit contains reagents for performing a four-base sequence determination on one or both strands of the target DNA. One-stranded sequence determination could be performed all in the 3'-direction, all in the 5'-direction, or as a combination of the two strands.

DETAILED DESCRIPTION OF THE INVENTION

Figure 1:
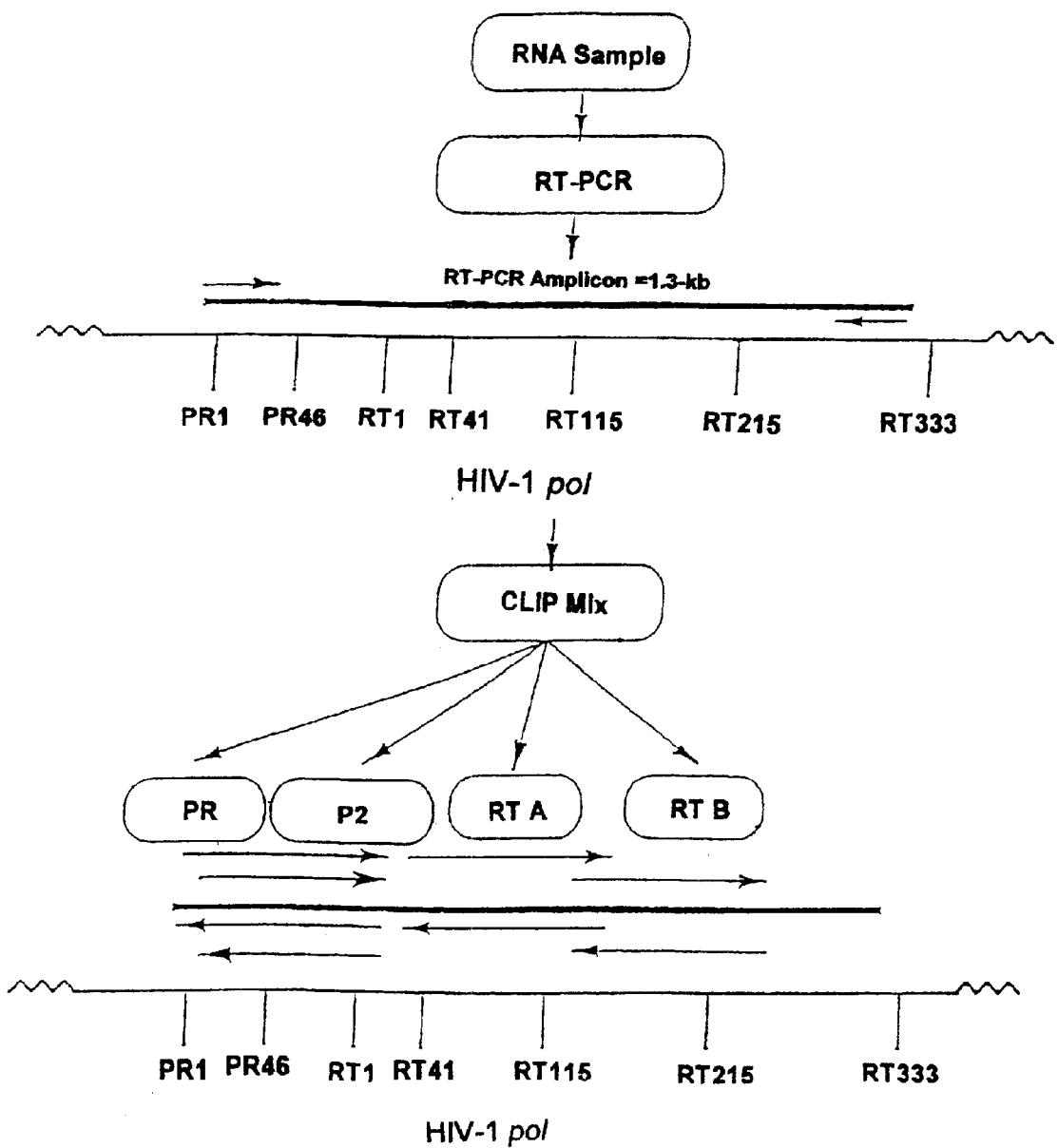
FIG. 1 shows a schematic representation of the invention.

While the terminology used in this application is standard within the art, the following definitions of certain terms are provided to assure clarity.

1. "Allele" refers to a specific version of a nucleotide sequence at a polymorphic genetic locus.
2. "Polymorphic site" means a given nucleotide location in a genetic locus which is variable within a population.
3. "Gene" or "Genetic locus" means a specific nucleotide sequence within a given genome.
4. The "location" or "position" of a nucleotide in a genetic locus means the number assigned to the nucleotide in the gene, generally taken from the cDNA sequence or the genomic sequence of the gene.
5. The nucleotides Adenine, Cytosine, Guanine and Thymine are sometimes represented by their designations of A, C, G or T, respectively. Dideoxynucleotides which are used as chain terminators are abbreviated as ddA, ddC, ddG and ddT.

While it has long been apparent to persons skilled in the art that knowledge of the identity of the base at a particular location within a polymorphic genetic locus may be sufficient to determine the allelic type of that locus, this knowledge has not led to any modification of sequencing procedures. Rather, the knowledge has driven development of techniques such as allele-specific hybridization assays, and allele-specific igation assays. Despite the failure of the art to recognize the possibility, however, it is not always necessary to determine the sequence of all four nucleotides of a polymorphic genetic locus in order to determine which allele is present in a specific patient sample. As disclosed generally in International Patent Publication No. WO 97/23650, certain alleles of a genetic locus may be distinguishable on the basis of identification of the location of less than four, and often only one nucleotide. This finding allows the development of the present method for improved allele identification within the highly polymorphic HIV genome.

Traditionally, if sequencing were going to be used to evaluate the allelic type of a poly-morphic gene, four dideoxy nucleotide "sequencing" reactions of the type described by Sanger et al. (Proc. Natl. Acad. Sci. USA 74: 5463–5467 (1977)) would be run on the sample concurrently, and the products of the four reactions would then be analyzed by polyacrylamide gel electrophoresis. (see Chp 7.6, Current Protocols in Molecular Biology, Eds. Ausubel, F. M. et al, (John Wiley & Sons; 1995)) In this well-known technique, each of the four sequencing reactions generates a plurality of primer extension products, all of which end with a specific type of dideoxynucleotide. Each lane on the electrophoresis gel thus reflects the positions of one type of base in the extension product, but does not reveal the order and type of nucleotides intervening between the bases of this specific type. The information provided by the four lanes is therefore combined in known sequencing procedures to arrive at a composite picture of the sequence as a whole.

In the method of the invention the sequence of a good portion of the diagnostically relevant protease and reverse transcriptase genes is obtained in three steps: 1) cDNA is generated from the RNA present in the sample, and amplified, preferably across a region extending from 6 codons before the protease up to codon 335 of the reverse transcriptase of HIV-1 (the primer regions are not included in this range). 2) Sequencing reactions are performed. 3)

Finally, the sequencing ladders are analyzed, preferably using the OpenGene™ System: the MicroGene Clipper™ or Long-Read Tower™ DNA Sequencers, GeneObjects™ and GeneLibrarian™ Software.

FIG. 1 shows one embodiment of the method of the invention schematically. As shown, an RNA sample is obtained and treated by reverse transcriptase-PCR (RT-PCR) to produce an amplicon of approximately 1.3 kbase pairs spanning the protease and reverse transcriptase genes of the HIV genome from a target cell. This reaction can be performed using, for example, the TITAN™ One-Tube RT-PCR system from Boehringer Mannheim (Cat. No. 1 855 476 or 1 882 382) using the following primers:

```
forward primer set:
AAGCAGGAGC CGATAGACAA GG        SEQ ID No. 1
AAGCAGGAGC HGAWAGACAR GG        SEQ ID No. 2
CAGCAGGAAC CGAGGGACAA GG        SEQ ID No. 3
reverse primer set:
CTAYTARGTC TTTTGWTGGG TCATA     SEQ ID No. 4
GCTATTAAGT CTTTTGATGG GTCA      SEQ ID No. 5
```

This amplicon is then combined with a master sequencing mixture containing buffer (260 mM Tris-HCL, pH 8.3; 32.5 mM MgCl$_2$ at 25° C.) and a polymerase enzyme such as Taq FS (Perkin Elmer/Applied Biosystems Cat No. 402070) This polymerase has a high rate of incorporation of dideoxynucleotide relateive to the incorporation rate of, for example, conventional Taq polymerase. This mixture is used as stock in the subsequent reactions.

The sequence reaction is performed on the protease gene using the following primers:

```
forward primers:
GAGCCRATAG ACAAGGAAYT RTAT      SEQ ID No. 6
GAGMCGATAG ACAAGGRVCT GTAT      SEQ ID No. 7
reverse primers:
ACTTTTGGGC CATCCATTCC T         SEQ ID No. 3
```

Other forward primers which could be used at this step include:

```
GAGCCGATAG ACAAGGAACT ATATCC    SEQ ID No. 9
GAGCCGATAG ACAAGGAAGT ATATCC    SBQ ID No. 10
GAGCCGATAG ACAAGGAAAT ATATCC    SBQ ID No. 11
GAGCCGATAG ACAAGGAACT GTATCC    SEQ ID No. 12
GAGCCGATAG ACAAGGAAGT GTATCC    SEQ ID No. 13
GAGCCGATAG ACAAGGAAAT GTATCC    SEQ ID No. 14
GAGCCGATAG ACAAGGGACT GTATCC    SBQ ID No. 15
GAGCCGATAG ACAAGGACCT GTATCC    SEQ ID No. 16
GAGCCGATAG ACAAGGGCCT GTATCC    SEQ ID No. 17
GAGCCGATAG ACAAGGAGCT GTATCC    SBQ ID No. 18
GAGCCGATAG ACAAGGGGCT GTATCC    SEQ ID No. 19
```

For the reverse transcriptase gene, three sets of primers are used as follows:

```
RTI Primers forward:
GTTAAACAAT GGCCATTGAC AGAAGA    SEQ ID No. 20
reverse:
GGAATATTGC TGGTGATCCT TTCC      SEQ ID No. 21 alternate forward:
GTTAAACAAT GGCCATTGAC AG        SEQ ID No. 22
RT2 Primers forward:
GAAGTATACT GCATTTACCA TACCTAG   SEQ ID No. 23
GAAGTATACT GCATTTACTA TACCTAG   SEQ ID No. 24
AAAGTATACT GCATTCACCA TACCTAG   SEQ ID No. 25
GAAATATACC GCATTTACCA TAYCTAG   SEQ ID No. 26
reverse:
TCTGTATGTC ATTGACAGTC CAGC      SEQ ID No. 27
alternate reverse:
TCTGTATATC ATTGACAGTC CAGT      SEQ ID No. 23
TCTGTATATC ATTGACAGTC CAGC      SEQ ID No. 29
TTCTGTATGT CATTGACAGT CCAGC     SEQ ID No. 30
P2 Primers forward:
TTCCCTCAGA TCACTCTTTG G         SEQ ID No. 31
TTCCCTCAAA TCACTCTTTG G         SEQ ID No. 32
reverse:
ACTTTTGGGC CATCCATTCC T         SEQ ID No. 33
```

The P2 forward primers are nested within the PR forward primers to sequence samples which do not sequence with the PR primers. When a sequencing device is employed which is capable of detecting and distinguishing two different fluorescent dyes (such as, for example, the Visible Genetics Inc. MicroGene Clipper or Long-Read Tower sequencers), both the forward and reverse primers are preferably each labeled with one of the two dyes. Forward and reverse sequencing fragments are then generated by thermally cycling the sample through multiple thermal cycles in the presence of either ddA, ddT, ddC and ddG. Analysis of the sequencing fragments produced using gel electrophoresis will allow the determination of the positions of all 4 bases.

Finally, if the intermediate test fails to provide unambiguous identification of the DNA type, sequencing of both strands may be performed. Again, the same sequencing primers identified above are used. Forward and reverse sequencing fragments can be produced in a single reaction using distinctively labeled forward and reverse primers, or in separate reactions depending on the nature of the detection system being employed.

Reagents suitable for practicing the method of the invention are suitably packaged in kit form. Thus, the invention provides a kit for analyzing the genetic type of an HIV-1 gene in a sample comprising: a kit for performing four base sequencing on HIV-1 comprising a plurality of A, C, G and T terminations mixtures, each of said termination mixtures including one of a plurality of primer pairs, each pair flanking a different region of the HIV-1 genome, the pairs together flanking substantially all of the protease and reverse transcriptase genes, and at least one member of each pair being labeled with a detectable label. Additional subkits for performing four base sequencing may be included when intermediate and final assays on one strand and both strands are desired.

As used herein, the term "termination mixture" refers to a mixture containing a mixture of the four deoxunucleotide triphosphates (dATP, dCTP, dGTP, and dTTP), one species of chain terminating dideoxynucleotide (ddATP, ddCTP, ddGTP or ddTTP) and the appropriate sequencing primers.

The subkit for performing A and T sequencing on HIV-1 may also be provided separately for performing the initial determination of only the A and T nucleotides. A preferred kit of this type, whether provided separately or as part of a kit for performing a hierarchical assay has primer pairs in which each primer is labeled with a different an spectroscopically distinguishable fluorescent dye, such as Cy5.0 and Cy5.5 and includes only one of the two possible types of termination mixtures, for example just the T termination mixture.

The following examples are included to illustrate aspects of the instant invention and are not intended to limit the invention in any way.

EXAMPLE 1

The RT-PCR is done on the HIV-1 RNA using a blend of enzymes forming RT-PCR Master Mixes described below to conduct six RT-PCT reactions. This RT-PCR is done on the RNA preparation obtained using the QIAmp Viral RNA kit from Qiagen. It can also be done on the RNA extract for the NucliSense™ (formerly known as NASBA) HIV Viral Load from Organon Teknica.

All the reagents, tubes, tips, and other material needs to be RNase-free. The recipe is made for 8 reactions (one strip of 8 tubes), including 10% extra. Thaw the RNA sample from the Amplicor HIV Monitor Test and keep on ice. This is the material obtained at step 14 of the section B "Specimen Preparation". If using RNA prepared for the NucliSense Assay, proceed the same way: thaw it and keep it on ice.

Take a 0.2 ml sterile, RNase-free, centrifuge tube, RNase-free, and prepare the RT-PCR Master Mix I (enough for 6 tubes, i.e. 6 samples) by adding the following ingredient in the order listed:

RT-PCR MASTER MIX I

7 µl of 80 mM DTT
10.5 µl of RNase-free dNTP at 10 mM each dNTP
21 µl of forward PCR primer at 28 µM.
21 µl of reverse PCR primer at 28 µM
3.5 µl of Rnase-inhibitor from Roche Molecular Biochemicals, catalog #799 025 (10,000 U)

Take a 0.2 ml sterile, RNase-free, centrifuge tube, RNase-free, and prepare the RT-PCR Master Mix II (enough for 6 tubes) by adding the following ingredient in the order listed:

RT-PCR MASTER MIX II

70 µl of 4×RT-PCR Buffer (280 mM Tris Hcl, 9.2 mM $MgCl_2$, 60 mM $(NH_4)_2SO_4$, 100 µg/ml Acetylated BSA from Life Tech, CA, pH 8.60 at 25° C.)
3.5 µl of RNase Inhibitor at 40 U/µl
7 µl of Superscript II
8.75 µl of Expand High Fidelity Enzyme System Enzyme Mix from Roche Molecular Biochemicals, catalog #17333 818
8.75 µl of AmpliTaq from Roche Molecular Systems.

Take one strip of 6 thin wall tubes. Add 9 µl of MASTER MIX I in each tube.

Add 17 µl of sample (RNA) to each tube. You may want to add a negative control per experiment.

Heat the RNA sample at 90° C. for 2 min. using the program below:, cool at 50° C. and add 14 µl of the MASTER MIX II in each tube (step 3 of the program below). Be careful not to cross contaminate your samples.

Start the RT-PCR. Use the heated lid. When using the MJ-Plates, indicate that tubes are used when asked by the PTC-200. The following is the programming for the PTC-200:
Calculated 1=90.0° for ever
2=90.0° for 2:00
3=50.0° for 1:00:00
4=94.0° for 2:00
5=1.0°/s to 94.0°
6=94.0° for 0:30
7=1.0°/s to 57.0°
8=57.0° for 0:30
9=1.0°/s to 68.0°
10=68.0° for 2:00
11=Goto 5, 19 times
12=1.0°/s to 94.0°
13=94.0° for 0:30
14=1.0°/s to 60.0°
15=60.0° for 0:30
16=1.0°/s to 68.0°
17=68.0° for 2:30
18=Goto 12, 16 times
19=68.0° for 7:00
20=4.0° for ever
21=End

EXAMPLE 2

To determine the sequence of amplicon, 7 µl of each terminator mix (16 when using a two dye instrument) are combined with a 5 ul of a master mix as follows:

MASTER MIX (two-dye system) for 6 tubes, i.e. for 6 samples:
120 µl of buffer (260 mM Tris-HCl, pH 8.3 at 29° C., 32.5 mM $MgCl_2$)
475 µl of sterile water
22.5 µl enzyme blend of AmpliTaq FS from Roche Molecular Systems 15 U/µl and 27 U/µl pyrophosphotase
5 µl of the PCR product from Example 3 per tube.

The two mixtures are mixed gently with a pipette tip, and the thermocylcing reaction is started. The following is the programming for the PTC-200:
Calculated 1=94.0° for 5:00
2=1.0°/s to 94.0°
3=94.0° for 0:20
4=1.0°/s to 56.0°
5=56.0° for 0:20
6=1.0°/s to 70.0°
7=70.0° for 1:30
8=Goto 2, 29 times
9=70.0° for 5:00
10=4.0° for ever
11=End Termination Mixes for Two Dye Systems
Protease A-Mix: 1.07 µM ddATP; 643 µM dATP; 643 µM dCTP; 643 µM dGTP; 643 µM dTTP;
330 nM total of forward primers and 330 nM total of reverse primers; 1 mM Tris-HCl, pH 8.0 at 25° C., 0.1 mM EDTA.
C-Mix: 2.14 µM ddCTP; 643 µM dATP; 643 µM dCTP; 643 µM dGTP; 643 µM dTTP;
330 nM total of forward primers and 330 nM total of reverse primers; 1 mM Tris-HCl, pH 8.0 at 25° C., 0.1 mM EDTA.
G-Mix: 2.14 µM ddGTP; 643 µM dATP; 643 µM dCTP; 643 µM dGTP; 643 µM dTTP;
330 nM total of forward primers and 330 nM total of reverse primers; 1 mM Tris-HCl, pH 8.0 at 25° C., 0.1 mM EDTA.

T-Mix: 2.14 μM ddTTP; 643 μM dATP; 643 μM dCTP; 643 μM dGTP; 643 μM dTTP;
330 nM total of forward primers and 330 nM total of reverse primers; 1 mM Tris-HCl, pH 8.0 at 25° C., 0.1 mM EDTA.

Both primers are labeled, for example with Cy5.0 and Cy5.5, respectively.

First RT region
A-Mix: 1.07 μM ddATP; 643 μM dATP; 643 μM dCTP; 643 μM dGTP; 643 μM dTTP;
330 nM total of forward primers and 330 nM total of reverse primers; 1 mM Tris-HCl, pH 8.0 at 25° C., 0.1 mM EDTA.
C-Mix: 2.14 μM ddCTP; 643 μM dATP; 643 μM dCTP; 643 μM dGTP; 643 μM dTTP;
330 nM total of forward primers and 330 nM total of reverse primers; 1 mM Tris-HCl, pH 8.0 at 25° C., 0.1 mM EDTA.
G-Mix: 2.14 μM ddGTP; 643 μM dATP; 643 μM dCTP; 643 μM dGTP; 643 μM dTTP;
330 nM total of forward primers and 330 nM total of reverse primers; 1 mM Tris-HCl, pH 8.0 at 25° C., 0.1 mM EDTA.
T-Mix: 2.14 μM ddTTP; 643 μM dATP; 643 μM dCTP; 643 μM dGTP; 643 μM dTTP;
330 nM total of forward primers and 330 nM total of reverse primers Both primers are labeled, for example with Cy5.0 and Cy5.5, respectively.

Second reverse transcriptase region

A-Mix: 1.07 μM ddATP; 643 μM dATP; 643 μM dCTP; 643 μM dGTP; 643 μM dTTP;
330 nM total of forward primers and 330 nM total of reverse primers
C-Mix: 2.14 μM ddCTP; 643 μM dATP; 643 μM dCTP; 643 μM dGTP; 643 μM dTTP;
330 nM total of forward primers and 330 nM total of reverse primers
G-Mix: 2.14 μM ddGTP; 643 μM dATP; 643 μM dCTP; 643 μM dGTP; 643 μM dTTP;
330 nM total of forward primers and 330 nM total of reverse primers
T-Mix: 2.14 μM ddTTP; 643 μM dATP; 643 μM dCTP; 643 μM dGTP; 643 μM dTTP;
330 nM total of forward primers and 330 nM total of reverse primers Both primers are labeled, for example with Cy5.0 and Cy5.5, respectively.

P2 protease region
A-Mix: 1.07 μM ddATP; 643 μM dATP; 643 μM dCTP; 643 μM dGTP; 643 μM dTTP;
330 nM total of forward primers and 330 nM total of reverse primers
C-Mix: 2.14 μM ddCTP; 643 μM dATP; 643 μM dCTP; 643 μM dGTP; 643 μM dTTP;
330 nM total of forward primers and 330 nM total of reverse primers
G-Mix: 2.14 μM ddGTP; 643 μM dATP; 643 μM dCTP; 643 μM dGTP; 643 μM dTTP;
330 nM total of forward primers and 330 nM total of reverse primers
T-Mix: 2.14 μM ddTTP; 643 μM dATP; 643 μM dCTP; 643 μM dGTP; 643 μM dTTP;
330 nM total of forward primers and 330 nM total of reverse primers Both primers are labeled, for example with Cy5.0 and Cy5.5, respectively.

---

We claim:

1. A kit for performing sequencing on an HIV-1 gene, comprising a plurality of termination mixtures, each of said termination mixtures including one of a plurality of primer pairs, said primer pairs together flanking essentially all of the protease gene and essentially all of the reverse transcriptase gene, and at least one member of each pair being labeled with a detectable label.

2. The kit according to claim 1, wherein the primers in each primer pair are labeled with different and spectroscopically distinguishable fluorescent labels.

* * * * *

SEQUENCE LISTING

```
<160> NUMBER OF SEQ ID NOS: 33

<210> SEQ ID NO 1
<211> LENGTH: 22
<212> TYPE: DNA
<213> ORGANISM: Human immunodeficiency virus
<220> FEATURE:
<223> OTHER INFORMATION: amplification primer for HIV

<400> SEQUENCE: 1
aagcaggagc cgatagacaa gg                                            22

<210> SEQ ID NO 2
<211> LENGTH: 22
<212> TYPE: DNA
<213> ORGANISM: Human immunodeficiency virus
<220> FEATURE:
<223> OTHER INFORMATION: amplification primer for HIV

<400> SEQUENCE: 2
aagcaggagc hgawagacar gg                                            22

<210> SEQ ID NO 3
<211> LENGTH: 22
<212> TYPE: DNA
```

```
<213> ORGANISM: Human immunodeficiency virus
<220> FEATURE:
<223> OTHER INFORMATION: amplification primer for HIV

<400> SEQUENCE: 3
cagcaggaac cgagggacaa gg                                              22

<210> SEQ ID NO 4
<211> LENGTH: 25
<212> TYPE: DNA
<213> ORGANISM: Human immunodeficiency virus
<220> FEATURE:
<223> OTHER INFORMATION: amplification primer for HIV

<400> SEQUENCE: 4
ctaytargtc ttttgwtggg tcata                                           25

<210> SEQ ID NO 5
<211> LENGTH: 24
<212> TYPE: DNA
<213> ORGANISM: Human immunodeficiency virus
<220> FEATURE:
<223> OTHER INFORMATION: amplification primer for HIV

<400> SEQUENCE: 5
gctattaagt cttttgatgg gtca                                            24

<210> SEQ ID NO 6
<211> LENGTH: 24
<212> TYPE: DNA
<213> ORGANISM: Human immunodeficiency virus
<220> FEATURE:
<223> OTHER INFORMATION: sequencing primer for protease gene

<400> SEQUENCE: 6
gagccratag acaaggaayt rtat                                            24

<210> SEQ ID NO 7
<211> LENGTH: 24
<212> TYPE: DNA
<213> ORGANISM: Human immunodeficiency virus
<220> FEATURE:
<223> OTHER INFORMATION: sequencing primer for protease gene

<400> SEQUENCE: 7
gagmcgatag acaaggrvct gtat                                            24

<210> SEQ ID NO 8
<211> LENGTH: 21
<212> TYPE: DNA
<213> ORGANISM: Human immunodeficiency virus
<220> FEATURE:
<223> OTHER INFORMATION: sequencing primer for protease gene

<400> SEQUENCE: 8
acttttgggc catccattcc t                                               21

<210> SEQ ID NO 9
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 9
gagccgatag acaaggaact atatcc                                          26
```

<210> SEQ ID NO 10
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 10
gagccgatag acaaggaagt atatcc                                          26

<210> SEQ ID NO 11
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 11
gagccgatag acaaggaaat atatcc                                          26

<210> SEQ ID NO 12
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 12
gagccgatag acaaggaact gtatcc                                          26

<210> SEQ ID NO 13
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 13
gagccgatag acaaggaagt gtatcc                                          26

<210> SEQ ID NO 14
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 14
gagccgatag acaaggaaat gtatcc                                          26

<210> SEQ ID NO 15
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 15
gagccgatag acaagggact gtatcc                                          26

<210> SEQ ID NO 16
<211> LENGTH: 26
<212> TYPE: DNA
<213> ORGANISM: Human immunodeficiency virus
<220> FEATURE:

```
<223> OTHER INFORMATION: sequencing primer for protease gene

<400> SEQUENCE: 16
gagccgatag acaaggacct gtatcc                                              26

<210> SEQ ID NO 17
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 17
gagccgatag acaagggcct gtatcc                                              26

<210> SEQ ID NO 18
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 18
gagccgatag acaaggagct gtatcc                                              26

<210> SEQ ID NO 19
<211> LENGTH: 26
<212> TYPE: DNA
<213> ORGANISM: Human immunodeficiency virus
<220> FEATURE:
<223> OTHER INFORMATION: sequencing primer for protease gene

<400> SEQUENCE: 19
gagccgatag acaagggget gtatcc                                              26

<210> SEQ ID NO 20
<211> LENGTH: 26
<212> TYPE: DNA
<213> ORGANISM: Human immunodeficiency virus
<220> FEATURE:
<223> OTHER INFORMATION: RT1 forward primer

<400> SEQUENCE: 20
gttaaacaat ggccattgac agaaga                                              26

<210> SEQ ID NO 21
<211> LENGTH: 24
<212> TYPE: DNA
<213> ORGANISM: Human immunodeficiency virus
<220> FEATURE:
<223> OTHER INFORMATION: RT1 reverse primer

<400> SEQUENCE: 21
ggaatattgc tggtgatcct ttcc                                                24

<210> SEQ ID NO 22
<211> LENGTH: 22
<212> TYPE: DNA
<213> ORGANISM: Human immunodeficiency virus
<220> FEATURE:
<223> OTHER INFORMATION: RT1 forward primer

<400> SEQUENCE: 22
gttaaacaat ggccattgac ag                                                  22
```

```
<210> SEQ ID NO 23
<211> LENGTH: 27
<212> TYPE: DNA
<213> ORGANISM: Human immunodeficiency virus
<220> FEATURE:
<223> OTHER INFORMATION: RT2 forward sequencing primer

<400> SEQUENCE: 23
gaagtatact gcatttacca tacctag                                              27

<210> SEQ ID NO 24
<211> LENGTH: 27
<212> TYPE: DNA
<213> ORGANISM: Human immunodeficiency virus
<220> FEATURE:
<223> OTHER INFORMATION: RT2 forward pimer

<400> SEQUENCE: 24
gaagtatact gcatttacta tacctag                                              27

<210> SEQ ID NO 25
<211> LENGTH: 27
<212> TYPE: DNA
<213> ORGANISM: Human immunodeficiency virus
<220> FEATURE:
<223> OTHER INFORMATION: RT2 forward primer

<400> SEQUENCE: 25
aaagtatact gcattcacca tacctag                                              27

<210> SEQ ID NO 26
<211> LENGTH: 27
<212> TYPE: DNA
<213> ORGANISM: Human immunodeficiency virus
<220> FEATURE:
<223> OTHER INFORMATION: RT2 forward primer

<400> SEQUENCE: 26
gaaatatacc gcatttacca tayctag                                              27

<210> SEQ ID NO 27
<211> LENGTH: 24
<212> TYPE: DNA
<213> ORGANISM: Human immunodeficiency virus
<220> FEATURE:
<223> OTHER INFORMATION: RT2 reverse primer

<400> SEQUENCE: 27
tctgtatgtc attgacagtc cagc                                                 24

<210> SEQ ID NO 28
<211> LENGTH: 24
<212> TYPE: DNA
<213> ORGANISM: Human immunodeficiency virus
<220> FEATURE:
<223> OTHER INFORMATION: RT2 reverse primer

<400> SEQUENCE: 28
tctgtatatc attgacagtc cagt                                                 24

<210> SEQ ID NO 29
<211> LENGTH: 24
<212> TYPE: DNA
<213> ORGANISM: Human immunodeficiency virus
<220> FEATURE:
<223> OTHER INFORMATION: RT2 reverse primer
```

-continued

```
<400> SEQUENCE: 29
tctgtatatc attgacagtc cagc                                          24

<210> SEQ ID NO 30
<211> LENGTH: 25
<212> TYPE: DNA
<213> ORGANISM: Human immunodeficiency virus
<220> FEATURE:
<223> OTHER INFORMATION: RT2 reverse primer

<400> SEQUENCE: 30
ttctgtatgt cattgacagt ccagc                                         25

<210> SEQ ID NO 31
<211> LENGTH: 21
<212> TYPE: DNA
<213> ORGANISM: Human immunodeficiency virus
<220> FEATURE:
<223> OTHER INFORMATION: P2 forward primer

<400> SEQUENCE: 31
ttccctcaga tcactctttg g                                             21

<210> SEQ ID NO 32
<211> LENGTH: 21
<212> TYPE: DNA
<213> ORGANISM: Human immunodeficiency virus
<220> FEATURE:
<223> OTHER INFORMATION: P2 forward primer

<400> SEQUENCE: 32
ttccctcaaa tcactctttg g                                             21

<210> SEQ ID NO 33
<211> LENGTH: 21
<212> TYPE: DNA
<213> ORGANISM: Human immunodeficiency virus
<220> FEATURE:
<223> OTHER INFORMATION: P2 reverse primer

<400> SEQUENCE: 33
acttttgggc catccattcc t                                             21
```